(12) United States Patent
Colclough et al.

(10) Patent No.: US 10,390,954 B2
(45) Date of Patent: Aug. 27, 2019

(54) METHOD TO INTRODUCE AN IMPLANTABLE DEVICE TO FILL A BONE VOID WHILST MINIMISING PRESSURISATION

(71) Applicant: Biocomposites Limited, Keele, Staffordshire (GB)

(72) Inventors: John Warren Colclough, Keele (GB); Phillip Anthony Laycock, Keele (GB); John Joseph Cooper, Keele (GB); Russell David Waters, Keele (GB)

(73) Assignee: BIOCOMPOSITES LIMITED, Keele, Staffordshire (GB)

( * ) Notice: Subject to any disclaimer, the term of this patent is extended or adjusted under 35 U.S.C. 154(b) by 0 days.

(21) Appl. No.: 15/288,328

(22) Filed: Oct. 7, 2016

(65) Prior Publication Data

US 2017/0020673 A1    Jan. 26, 2017

Related U.S. Application Data

(63) Continuation-in-part of application No. 15/040,075, filed on Feb. 10, 2016.

(30) Foreign Application Priority Data

Feb. 17, 2015 (GB) .................................. 1502655.2

(51) Int. Cl.
*A61F 2/28* (2006.01)
*A61F 2/44* (2006.01)
(Continued)

(52) U.S. Cl.
CPC ............ *A61F 2/28* (2013.01); *A61B 17/7283* (2013.01); *A61B 17/921* (2013.01); *A61F 2/44* (2013.01); *A61F 2/4644* (2013.01); *A61L 27/025* (2013.01); *A61L 27/12* (2013.01); *A61L 27/54* (2013.01); *A61M 37/0069* (2013.01); *B29C 39/026* (2013.01); *B33Y 80/00* (2014.12); *A61F 2002/2835* (2013.01); *A61F 2002/2839* (2013.01); *A61F 2250/0067* (2013.01); *A61L 2300/404* (2013.01); *A61L 2300/414* (2013.01);

(Continued)

(58) Field of Classification Search
USPC .... 623/13.11–13.14, 23.7–23.75; 606/92–93
See application file for complete search history.

(56) References Cited

U.S. PATENT DOCUMENTS 6,045,555 A * 4/2000 Smith .................... A61F 2/4601
606/80
6,413,089 B1 * 7/2002 Ashman ............... A61C 8/0006
433/173

(Continued)

OTHER PUBLICATIONS

Dr. Laurence Knott; Fat Embolism Syndrome; Patient; patient.info/doctor/fat-embolism-syndrome.

(Continued)

*Primary Examiner* — Yashita Sharma
(74) *Attorney, Agent, or Firm* — Tarolli, Sundheim, Covell & Tummino LLP

(57) ABSTRACT

Disclosed is an invention that provides a method of treating a bone void of a patient through the use of an implantable device whilst minimising the potential for an increase in pressure within the bone void thus avoiding embolization of the void contents into the patient's bloodstream.

15 Claims, 8 Drawing Sheets

(51) Int. Cl.
  *B29C 39/02* (2006.01)
  *A61F 2/46* (2006.01)
  *A61M 37/00* (2006.01)
  *A61B 17/92* (2006.01)
  *B33Y 80/00* (2015.01)
  *A61L 27/02* (2006.01)
  *A61L 27/12* (2006.01)
  *A61L 27/54* (2006.01)
  *A61B 17/72* (2006.01)
  *B29L 31/00* (2006.01)

(52) U.S. Cl.
  CPC ..... *A61L 2300/416* (2013.01); *A61L 2430/02* (2013.01); *B29L 2031/7532* (2013.01)

(56) References Cited

U.S. PATENT DOCUMENTS

| | | | | |
|---|---|---|---|---|
| 2006/0200236 | A1* | 9/2006 | Bianchi | A61F 2/08 623/13.14 |
| 2007/0016163 | A1* | 1/2007 | Santini, Jr. | A61C 8/0012 604/500 |
| 2008/0195204 | A1* | 8/2008 | Zhukauskas | A61F 2/08 623/13.14 |
| 2015/0245879 | A1* | 9/2015 | Nikou | A61B 17/1764 606/88 |
| 2016/0136410 | A1* | 5/2016 | Aklog | A61M 1/3655 604/506 |

OTHER PUBLICATIONS

F. Hampson; Fat Embolism; J. Clin. Path., 23, Suppl. (Roy. Coll. Path.), 4, pp. 121-122.

Robello MM et al.; Venting Alone is Insufficient in Preventing Complications in the Prophylactic Nailing of Femoral Metastases; 49th Annual Meeting of the Orthopaedic Research Society, Poster #0997.

Nissar Shaikh; Emergency management of fat embolism syndrome; Journal of Emergencies, Trauma, and Shock; Jan.-Apr. 2009; 2(1); pp. 29-33.

Paul S. Issack et al.; Fat Embolism and Respiratory Distress Associated With Cemented Femoral Arthroplasty; The American Journal of Orthopedics; Feb. 2009; pp. 72-76.

Shamsuddin Akhtar, MD; Fat Embolism; Anesthesiology Clin (2009); pp. 533-550.

* cited by examiner

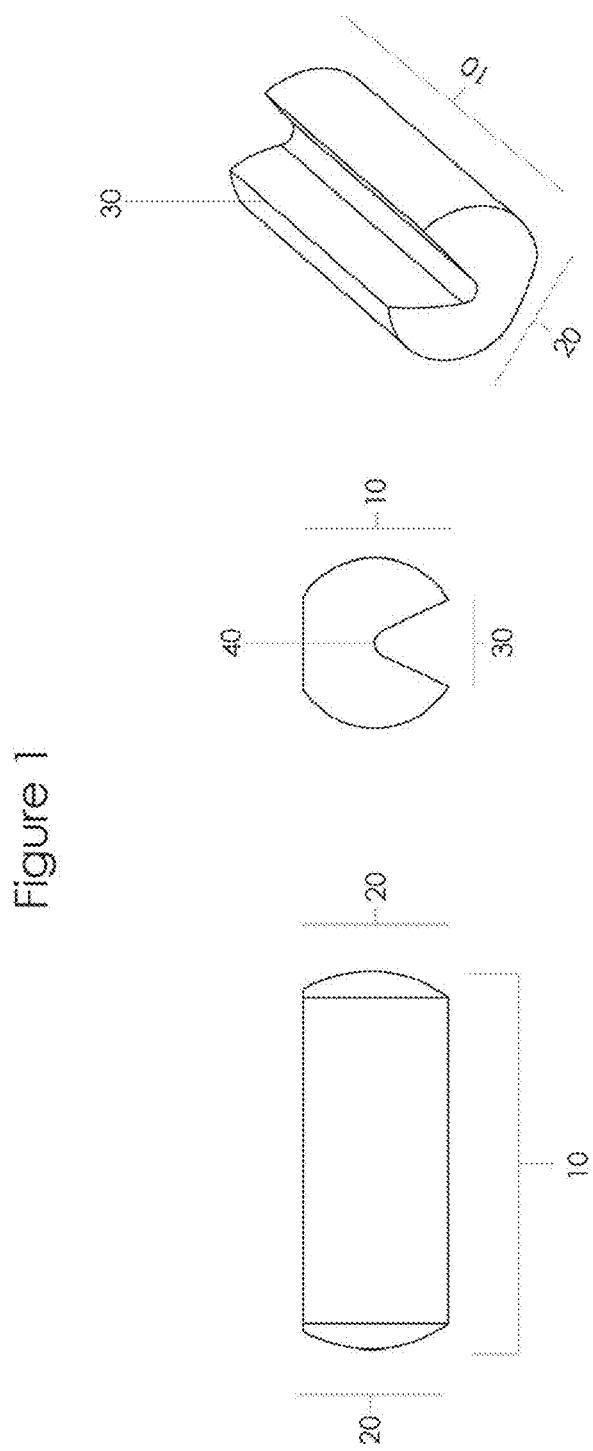

METHOD TO INTRODUCE AN IMPLANTABLE DEVICE TO FILL A BONE VOID WHILST MINIMISING PRESSURISATION

CROSS-REFERENCE TO RELATED APPLICATIONS

This application is a Continuation-in-Part of U.S. patent application Ser. No. 15/040,075, filed on Feb. 10, 2016, which claims priority to UK Patent Application No 1502655.2, filed on Feb. 17, 2015, all of which are hereby incorporated by reference in their entirety.

FIELD OF THE INVENTION

Bone substitute materials or bone void fillers are increasingly being used for reconstruction or treatment of bone voids or bone defects. The bone substitute material may be in any one of a number of physical forms including an injectable paste or putty formulation or solid forms such as granules, beads or pellets. During implantation it is essential for the surgeon to ensure that introduction of the bone substitute material into the bone void does not pressurise the void. Such pressurisation may cause an embolism where the void contents; air, bone marrow or the bone substitute material itself, are forced into the blood stream of a patient with potentially disastrous consequences to the patient.

The present invention provides a method of treating a bone void with an implantable device to be loaded into a void such as a long bone intramedullary canal (IM canal) whilst concurrently minimising the increase of pressure within the void, and hence minimising the risk of embolization of the void contents into the patient's bloodstream, which could have potentially fatal consequences for the patient.

BACKGROUND OF THE INVENTION

Certain clinical orthopaedic procedures often involve the insertion of a bone substitute material or a device in to a bone void or defect. The defect may be created by disease, surgically created or may have resulted from traumatic injury to the bone. A bone void or defect in, for example, a long bone IM canal may be prepared or created to accept an implantable device through either debridement, reaming out the contents of the canal or simply by the removal of an intra-medullary nail or rod. The purpose of the bone substitute material or a similar material may be to regenerate bone, to provide structural support or to be a carrier for the delivery of a therapeutic agent to the bone void.

Current practice is to use a bone substitute material that can be dispensed or inserted into the bone void by a number of means. For example, a material having the consistency of a paste can be inserted or injected in to the void or defect using a syringe or similar device. Granules, beads or pellets can be digitally inserted one at a time or they may be loaded into a delivery device for subsequent dispensation into the void. It is important not to occlude the entrance to the bone void during material or device insertion as blocking a vent path whilst inserting the material or device into a contained void will result in increasing pressurisation of the bone void. This increase in pressurisation within the bone void may result in embolization, such as a fat embolism of the void contents in to the blood stream of the patient with disastrous consequences. Fat embolism syndrome (FES) is caused by fat droplets which are then found within the peripheral and lung microcirculation[1]. FES is a serious complication and can result in the death of the patient.

The pathologic significance of FES was first noted in 1862 by Zenker; however, the first person considered to diagnose fat embolism was Von Bergmann in 1873, who reported on his findings concerning this condition[1, 4].

As patients are an aging population it means that the number of orthopaedic operations involving bone voids and more specifically the IM canal are increasing, thus increasing the risk of embolization or FES which in turn means an increase in perioperative cardiorespiratory emergencies[1].

Patients suffering from FES may be asymptomatic for a period of 12 to 48 hours before the clinical manifestations of the syndrome; these manifestations include but are not limited to tachycardia, petechial rash, elevated temperature (usually in excess of 38.3° C.), hypoxemia and also neurological symptoms[6].

The mortality rate for patients suffering from FES is from 5-15%[3]; however proper treatment of the patient through ensuring good arterial oxygenation, the restriction of fluids and the use of diuretics which assist in minimising the accumulation of fluid in the patient's lungs will assist in recovery.

A technique often employed by the treating surgeon in, for example, long bones or vertebral bodies to mitigate this problem is to provide a second hole known as a venting hole. In long bones this is usually done by drilling a secondary opening through the cortex into the medullary canal. This hole is usually placed distal to the hole which the surgeon created for the placement of the bone substitute material or device and provides an exit path which enables escape of the void contents ahead of the advancing bone substitute material.

This technique, however, has a number of problems. The bone substitute material which the surgeon injects or digitally packs into the long bone may escape through this venting hole. This therefore means that an insufficient amount of bone substitute material may remain within the void or IM canal while the escaped material may cause injury to the adjacent soft tissues[2]. Another issue found with this technique of drilling a venting hole through the cortical bone is that it can increase the risk of fracture at the site of the drilled hole.

Therefore, the problem to be solved is how to effectively and safely introduce an implantable device comprising a bone substitute material into a bone void, particularly a contained bone void such as the IM canal, whilst ensuring that the bone void does not become excessively pressurised.

SUMMARY OF THE INVENTION

The present invention provides a method of treating a bone void involving the insertion of an implantable device or devices in to said void, following preparation of the void, whilst ensuring that any increase in pressure during insertion is minimised by virtue of the geometric configuration of the implantable device or devices, thus assisting in the prevention of embolization of the void contents into the patient's blood stream.

DISCLOSURE OF THE INVENTION

Disclosed is a method of treating a bone void in a patient comprising the introduction into a bone void of one or more implantable devices, each of which one or more implantable devices contains a longitudinal channel where the longitudinal channel creates a venting path allowing for depressurisation of contents of the bone void.

When the one or more implantable devices are introduced into the bone void, the venting path allows the escape of a portion of the bone void contents, which helps to minimise the levels of pressurisation of the bone void contents.

The one or more implantable devices comprise a bone substitute material.

The bone void is particularly a contained bone void.

The method of treatment uses one or more implantable devices which may be sequentially or serially dispensed into the bone void and may be applied to the site digitally or by the use of an introducer following preparation of the bone void. The introducer may comprise a guide tube and 'pusher' and may be loaded with the one or more implantable devices in situ or may be pre-loaded with the implantable devices prior to insertion into the IM canal. The IM canal is prepared to accept the one or more implantable devices by, for example, reaming or by removal of an intramedullary nail. The one or more implantable devices are typically, but not necessarily, spherocylindrical or capsule shaped, i.e. substantially cylindrical, having convex, domed or semi-spherical shaped ends. A longitudinally aligned channel, or a plurality of longitudinally aligned channels, extends the full length of any single device. The implantable device may have one or more of the longitudinally aligned channels. The device may be used alone or in combination with similar devices.

The longitudinal channel(s) intersect the surface of the device and extend towards the device centreline. The depth of the longitudinal channel(s) may extend from the outer circumference to the axial centreline of the implantable device and is generally tapered such that the width of the longitudinal channel(s) opening on the outer, circumferential edge of the implantable device is greater than its width at its base, thus creating a continuous longitudinal channel or channels along the implantable device. The angular shaped longitudinal channel, or channels, of the implantable device preferably has an angle sized from about 10 degrees to about 145 degrees, more preferably about 20 degrees to about 50 degrees.

The continuous longitudinal channel(s) located longitudinally along the implantable device creates a venting path which allows for the exit of the void or IM canal contents as the implantable device(s) are inserted and/or advanced into the void or IM canal where they displace the contents of the void or the IM canal, thus allowing contents to escape the void or IM canal.

In one embodiment of the invention, for implantable devices that are produced using the mould of FIGS. 2A and 2B herein, the opposing longitudinal side of the implantable device has a flat surface, which further allows for the displacement and escape of the void or IM canal contents.

The implantable device of the present invention is preferably about 5 mm to about 25 mm in diameter, more preferably about 7 mm to about 12 mm.

The overall length of the implantable device is preferably from about 6 mm to about 300 mm, more preferably about 10 mm to about 100 mm.

However, it will be appreciated that the diameter and length of the device is dependent upon the size of the bone void it is to be inserted into.

The longitudinal channel preferably has a taper angle of 10 degrees to 145 degrees, more preferably about 20 degrees to about 50 degrees.

The implantable device(s) of the present invention can be formed by several methods, including but not limited to, casting the implantable device in a multi-cavity flexible mould mat, or 3D printing the implantable device. Once formed by one of the methods disclosed above, the device(s) are ready to be implanted into a void or IM canal in a patient. This may be accomplished by digitally packing or by means of an introducer comprising a non-rigid guide tube and pusher. The implantable device(s) can be serially (i.e. all together) or sequentially (i.e. one at a time) inserted in their axial orientation into the bone void or IM canal.

A guide tube can be inserted into the void or IM canal and then loaded with implantable devices. Alternatively, a guide tube can be first filled with one or more implantable devices, and the guide tube is subsequently inserted into the bone void or IM canal.

A non-rigid pusher can then be placed into the guide tube where it will make contact with the most proximal implantable device. The guide tube is then retracted whilst positive pressure is maintained on the pusher and the pusher maintains contact with the implantable device. This action will cause the implantable device(s) to be dispensed into the void or IM canal of the patient as the guide tube is retracted.

Alternatively, the devices may be digitally inserted into the void or IM canal of the patient by the surgeon.

By virtue of the geometric shape of the devices, the longitudinal channels of adjacent implantable devices do not need to be aligned with each other in order to provide a continuous venting path for the displacement and exit of the contents of the void or IM canal. This is due to the convex, domed or semispherical shaped ends of the implantable device which allow for the continuous flow of the contents of the void or IM canal to the adjacent implantable device.

Thus described is a method of treatment of a bone void: the method comprising preparation of the bone void followed by insertion, into the void, of one or more implantable devices designed to minimise any pressure build-up in the bone void or defect during the insertion procedure. The implantable device typically has a capsule shape; cylindrical with convex, domed or semispherical shaped ends, and a longitudinal channel or channels running end-to-end within the implantable device. The particular geometric features ensure a continuous venting path from the distal end of the first implantable device to the proximal end of the last implantable device. Thus, when serially inserted into a void or IM canal, it allows for the displacement of the void or IM canal contents via the venting path. The contents of the void or IM canal can be blood, marrow, fat, air, irrigation solution or any other fluid which may be present and occupy the void, partially or wholly, prior to insertion of the implantable device. The implantable device(s) are axially orientated for insertion into a void or IM canal where the presence of a continuous venting path is independent of the circumferential orientation of adjacent implantable devices. The implantable device may be made from bone substitute material and may include a medicament contained therein to provide a therapeutic function.

A range of bone substitute materials may be used in the present invention including, but not limited to, calcium-based bone substitute materials which may be used as bone void fillers and carriers for delivery of therapeutic agents to a bone void or defect. The bone substitute material, such as calcium sulfate, is typically supplied in the form of a powder which when mixed with a liquid component forms a hard-enable cohesive mass that can be moulded into shapes then allowed to cure undisturbed and finally set (solidify) to form an implantable device.

Also provided in accordance with the present invention is an arrangement of the implantable devices described herein, the arrangement comprising a plurality of the devices lined up end to end. As desired, the longitudinal channels may or may not be axially aligned with each other prior to, during or subsequent to insertion.

This arrangement of the devices of the present invention is to be inserted and used in the bone void e.g. IM canal of a patient.

According to a further embodiment of the invention, there is provided a method of making an implantable device as defined hereinabove, wherein the implantable device is made by either casting the implantable device in a mould, or by 3D printing.

Thus this method of treatment with the implantable device provides a continuous longitudinal channel which, during insertion, creates a venting path thus allowing for depressurisation of the bone void contents by virtue of their geometric construction, thus helping to avoid embolization into the patient's blood stream.

In certain embodiments the method can be directed to a method to treat a patient suffering from osteomyelitis in their long bone.

Osteomyelitis is an infection in the patient's bone, which can be caused through trauma, surgical intervention or haematogenous seeding, or by the presence of such devices as an orthopaedic pin, plate, nail or an Ilizarov fixation device. Patients with certain medical conditions may be more susceptible to osteomyelitis and these conditions may include but are not limited to immunosuppression, immunodeficiency virus (HIV), diabetes, cancer and sickle cell disease.

The treatment of osteomyelitis may include debridement and irrigation of the infected long bone leaving a bone void. The present invention allows for the treatment of the osteomyelitis in the patient by inserting the medicament impregnated implantable device following debridement and irrigation.

Another embodiment of the present invention is to fill a void in a long bone left by the removal of an IM nail. IM nails are used to treat fractures typically in long bones such as tibia or femur. IM nails may be removed due to complications suffered by the patient such as implant failure, pain or infection.

Upon the removal of an IM nail the patient is left with a void within their long bone. The surgeon may need to remove any necrotic tissue by reaming the IM canal leaving a bleeding site. Depending on the reason for the removal of the IM nail, the present invention will allow for the treatment of the bone void by inserting a medicament impregnated (if applicable) implantable device whilst allowing the void contents to exit the void via the present invention's venting path thus avoiding pressurisation of the void and prevention of FES.

Another embodiment of the present invention is to treat bone tumours in long bones. Once a bone tumour is removed within the long bone it will leave a void that will need to be filled as well as treated with the appropriate medicament. The bone void will need to have any affected tissue removed thus leaving healthy bleeding bone, the medicament impregnated implantable device can be placed in the void while still allowing the void contents to exit via the longitudinal channel of the implantable devices, which constitutes the venting path.

Definitions:

"Axial centreline" means an imaginary line through the centre of the device, extending along the length thereof and following an axis of symmetry.

"Bioresorbable" refers to a material which resorbs in the body.

"Bone substitute material" is a material used to fill a bone void, including but not limited to poly-methyl methacrylate (PMMA) and hydraulic setting materials which comprise calcium sulfate, calcium carbonate and calcium phosphate containing materials.

"Bone void filler" is a material used to fill a bone void, including but not limited to poly-methyl methacrylate (PMMA) and hydraulic setting materials which comprise calcium sulfate, calcium carbonate and calcium phosphate containing materials.

"Capsule" defines a geometric shape comprising a cylindrical body with convex ends, sometimes described as a spherocylinder.

"Capsule or Spherocylindrical" means a three dimensional shape where one or more surfaces are semispherical and another surface is cylindrical.

"Cavity" or "device cavity" means a cavity within a mould for producing a bone substitute material device.

"Channel" describes a gap in an object which generally extends the full length or width of the object and allows for the passage of fluid.

"Comprising" or any cognate word specifies the presence of stated features, steps, or integers or components, but does not preclude the presence or addition of one or more other features, steps, integers, components or groups thereof. The expressions; "consists of" or "consists essentially of" or cognates may be embraced within "comprises" or cognates, wherein "consists essentially of" permits inclusion of substances not materially affecting the characteristics of the composition to which it applies.

"Contained bone void" is a bone void or defect that has only one opening to atmosphere. The opening may be surgically created or created through trauma or disease.

"Debride" refers to the surgical removal of devitalized, necrotic or contaminated tissue.

"Digitally" means the placement of implantable devices into a void or IM canal by hand.

"Embolism" or "embolization" means to block or occlude blood vessels.

"Implantable device" describes a component for implantation into a void or IM canal which has a longitudinal channel which creates a venting path.

"Device mould" or "mould" describes a mould for the production of bone substitute material devices. It may contain one, or more preferably a plurality of cavities.

"Excessively pressurised" refers to a situation whereby the pressure within a bone void increases to a level high enough to cause an embolism.

"Fat embolism syndrome" (FES) is a medical condition where a fat particle or droplet passes into a patient's bloodstream and subsequently lodges within a blood vessel and blocks the blood vessel.

"Hardenable bone substitute material" describes a composition comprising a bone substitute material as defined herein and a hardening agent, e.g. an aqueous solution, which upon hardening (i.e. fully setting) forms bone void filler as defined herein. Typically, the hardenable bone substitute material is in the form of a workable paste.

"Hydraulic setting material" means a material which sets (solidifies) due to a chemical reaction between the dry ingredients and water.

"Intramedullary canal" (IM canal) refers to the inside of a bone, typically the marrow cavity of a long bone.

"Granules" describes irregularly sized and shaped, generally angular, solid or porous particles.

"IM Nail" includes intramedullary nails and an intramedullary rod.

"Long bone" means bones of a patient that provide strength, structure and mobility. Long bones are normally hard and dense and include but are not limited to the tibia, femur and humerus.

"Longitudinal" refers to a direction parallel to the long/cylindrical axis of the device.

"Longitudinal channel" describes an aligned channel or a plurality of channels that extends continuously the full length of the implantable device.

"Medicament" or "therapeutic agent" describes, but is not limited to antibiotics, antimycotics, bone morphogenetic proteins, nonsteroidal anti-inflammatory drugs (NSAIDS), antiresorptive agents, anti-androgens, cytostatic agents, antineoplastic drugs, bisphosphonates and analgesics.

"Mould" (noun) describes a tool with a hollow space or cavity which is used to impart the desired form to the product being moulded. The cavity or cavities are filled with a flowable material which subsequently hardens to produce solid components having a shape defined by the shape of the mould cavity.

"Mould mat" means a generally flat and flexible mould having a plurality of cavities to accept bone substitute material in a mouldable paste condition and contain the bone substitute material or cement therein for a time sufficient to allow hardening of the cement to give set (solidified) devices prior to their extraction.

"Non-rigid" describes the mechanical property of a material that allows it to bend or flex without fracture when a bending force is applied.

"NSAID" means a non-steroidal anti-inflammatory drug.

"Patient" means a human or animal subject that is receiving or is to receive medical treatment.

"Petechial rash" means round spots or pinpoints that appear on the skin of a human or animal subject as a result of bleeding occurring under the subject's skin.

"PMMA" means poly (methyl methacrylate).

"Semispherical" means 'not completely spherical' and describes a geometric shape which is formed when a sphere is intersected by a plane.

"Subject" is an entity receiving or needing to receive medical treatment.

"Surgeon" means a medical practitioner qualified to practise surgery on a human or animal subject.

"Venting path" describes a path created by the longitudinal channel of the implantable device which allows for the venting of the bone void contents.

BRIEF DESCRIPTION OF THE DRAWINGS

The various features of the invention, which are applicable as appropriate to all aspects, will now be described in more detail with reference to the following drawings, where:

FIG. 1 shows plan, end and isometric views of an implantable device for use in the instant invention with a spherocylindrical or capsule shape and a longitudinal channel.

DETAILED DESCRIPTION OF THE DRAWINGS

FIG. 1 shows an implantable device 10 of the present invention, which is capsule shaped, having domed, convex or semispherical shaped ends 20. A longitudinally aligned channel 30 intersects the surface of the implantable device and extends towards the cylindrical axis 40 of the implantable device.

Figure 2A:
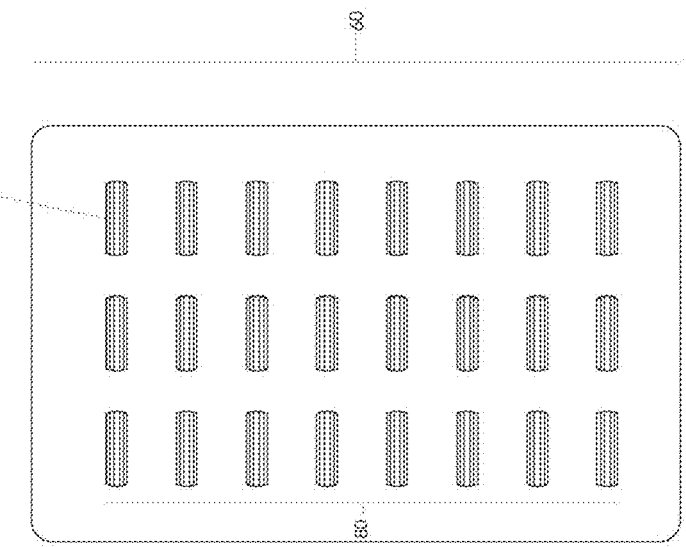
FIG. 2A shows a multi-cavity flexible mould mat with cavities that, when filled with bone substitute material, can be used to form the implantable device(s).

FIG. 2A shows a multi-cavity flexible mould mat 60 which has cavities 70 in rows 80. Each cavity has a shape that corresponds to the shape of the implantable device 10.

Figure 2B:
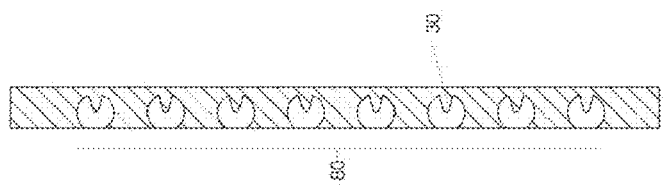
FIG. 2B shows a cross-section view of the multi-cavity flexible mould mat.

FIG. 2B shows a cross-sectional view of the multi-cavity flexible mould mat 60, of a row of cavities 80. The shape of the cavities 80 corresponds to that of the implantable devices 10, with the longitudinal channels 30 visible.

However, while the multi-cavity flexible mould mat 60 constitutes a typical method of manufacturing the implantable devices 10, the implantable devices 10 may be alternatively produced by a method not described herein, by methods which will be readily apparent to the person skilled in the art.

Figure 3A:
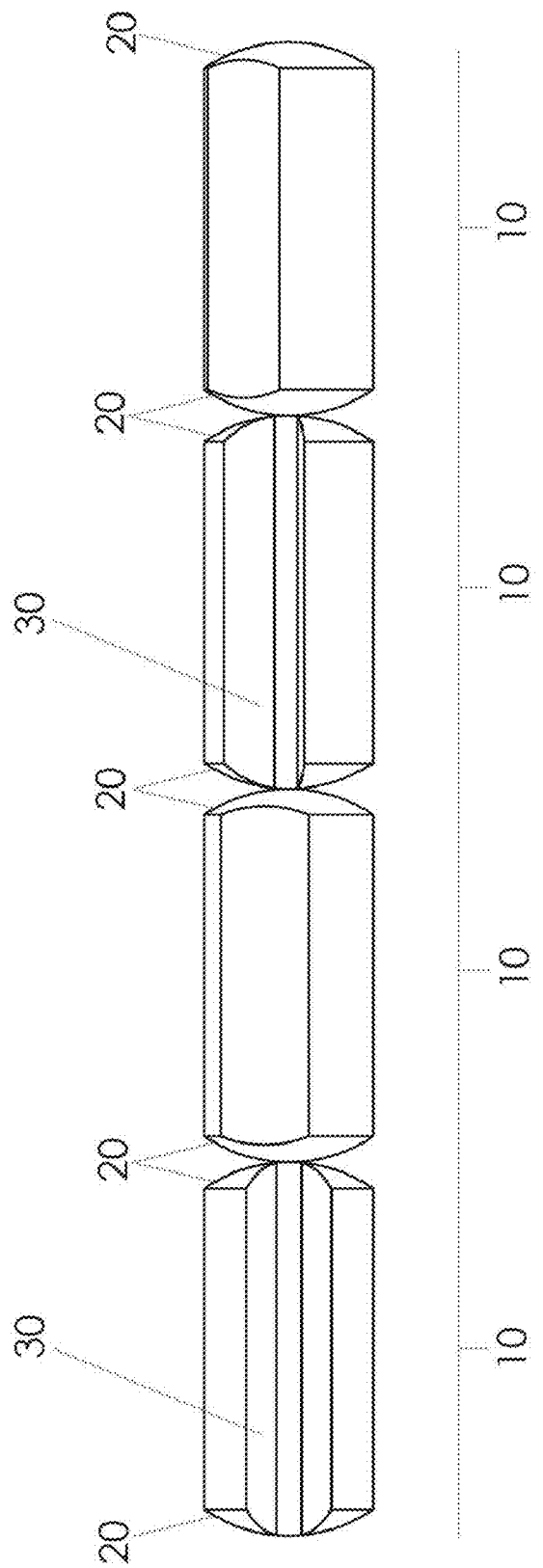
FIG. 3A shows multiple implantable devices of the present invention together in series.

FIG. 3A shows multiple implantable devices 10 of the present invention together in series, showing the longitudinal channels 30 for venting the contents of the bone void or IM canal which form part of the venting path 50 through the longitudinal channel 30 and domed, convex or semispherical shaped ends 20.

Figure 3B:
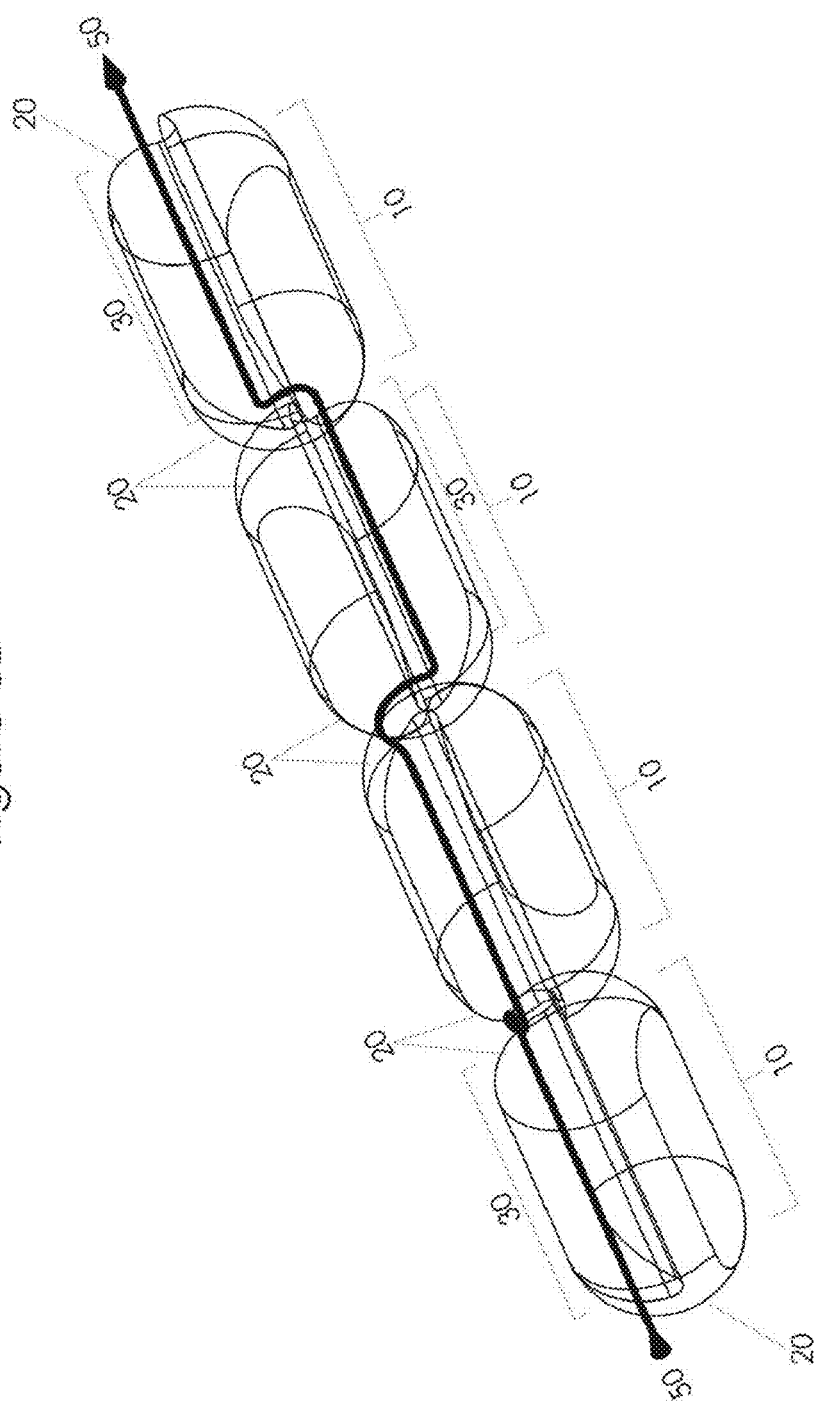
FIG. 3B shows multiple implantable devices of the present invention together in series. A 'venting path' is shown where the void contents may exit the bone void or the IM canal during device insertion, helping to minimise pressure build-up within the void and thus minimise the potential for an embolism.

FIG. 3B shows multiple implantable devices 10 of the present invention together in series. A continuous venting path 50 for the contents of the bone void or IM canal is shown through the longitudinal channels 30 and domed, convex or semispherical shaped ends 20, thus helping to minimise pressure build-up within the void and thus minimise the potential for an embolism.

Figure 4:
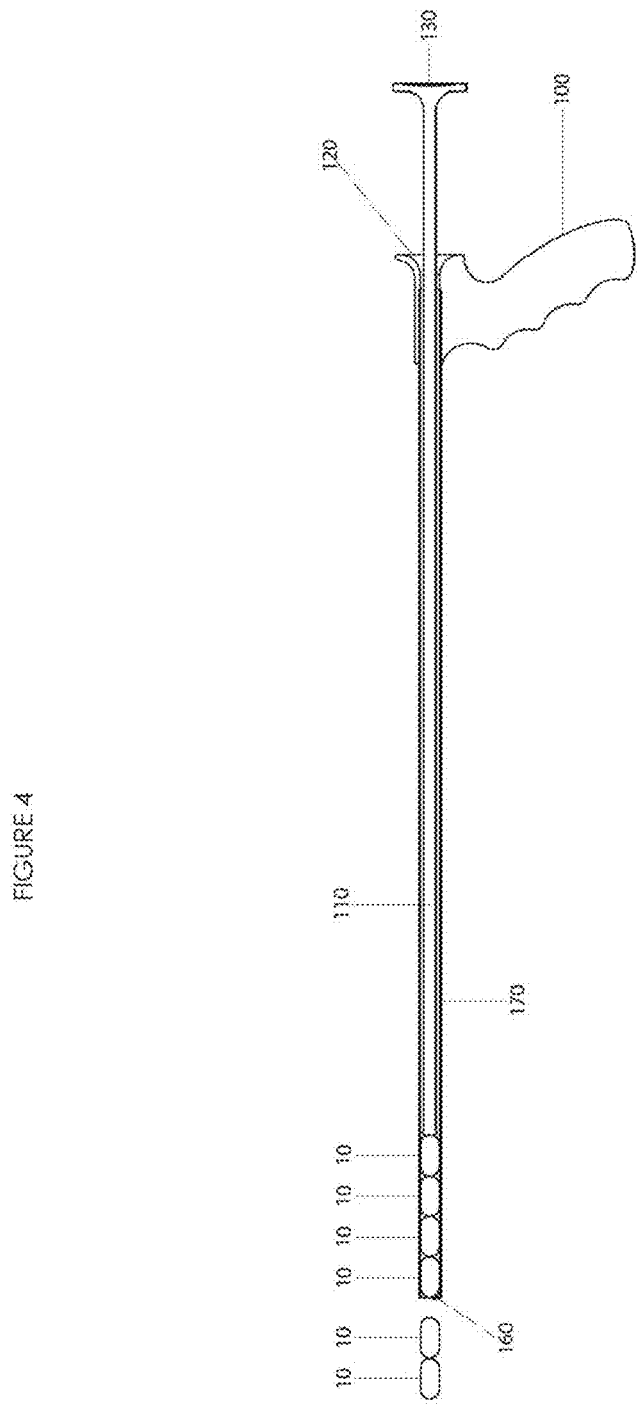
FIG. 4 shows an inserter (guide tube and engaged pusher) with implantable devices being dispensed.

FIG. 4 shows a guide tube 170 with a handle 100, for the insertion of the implantable devices in to the bone void or IM canal, and a funnel 120 at the proximal end to help guide insertion of the implantable devices 10 and subsequently the pusher 110. The outside diameter of the guide tube 170 is less than the inside diameter of the medullary canal to be treated. The distal end of the guide tube 170 has a flexible retainer 160 which retains the implantable devices 10 within the guide tube 170 until pressure is applied by the pusher 110 at its proximal end 130 to the implantable devices 10 which will cause the retainer 160 to flex allowing the implantable devices 10 to exist the guide tube 170 at its distal end.

Figure 5:
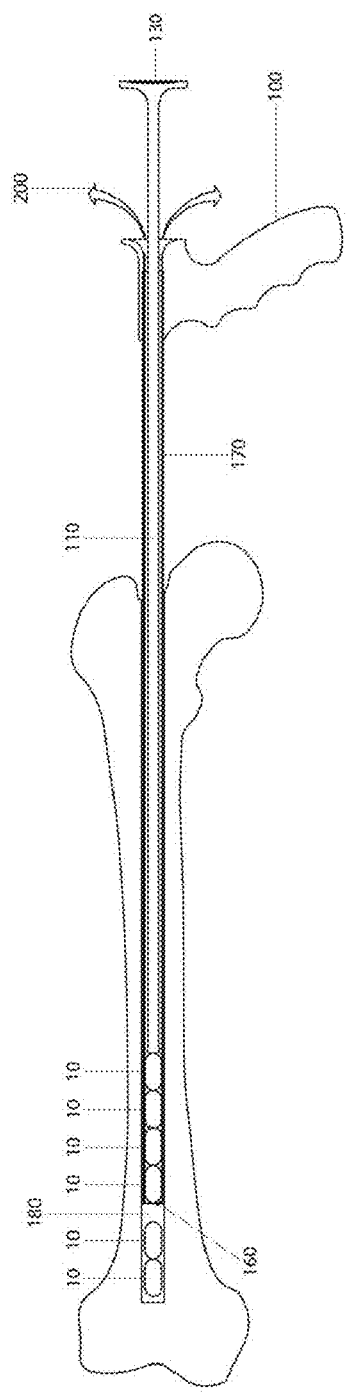
FIG. 5 shows an inserter being used to dispense implantable devices in to an intramedullary canal.

FIG. 5 shows a guide tube 170 and pusher 110, inserted into an IM canal 180 of a patient, where the outer diameter of the pusher 110 is less than the internal diameter of the guide tube 170. The pusher 110 has a circular handle 130 to allow the Surgeon to maintain pressure on the implantable devices 10 whilst retracting the guide tube 170 to dispense the devices 10 into the IM canal 180. The guide tube 170 has a flexible retainer 160 which retains the implantable devices 10 until the surgeon applies pressure on the pusher handle 130. Once pressure is applied by the surgeon the fluid contents 200 of the IM canal can be seen exiting the proximal end of the guide tube 170.

Figure 6:
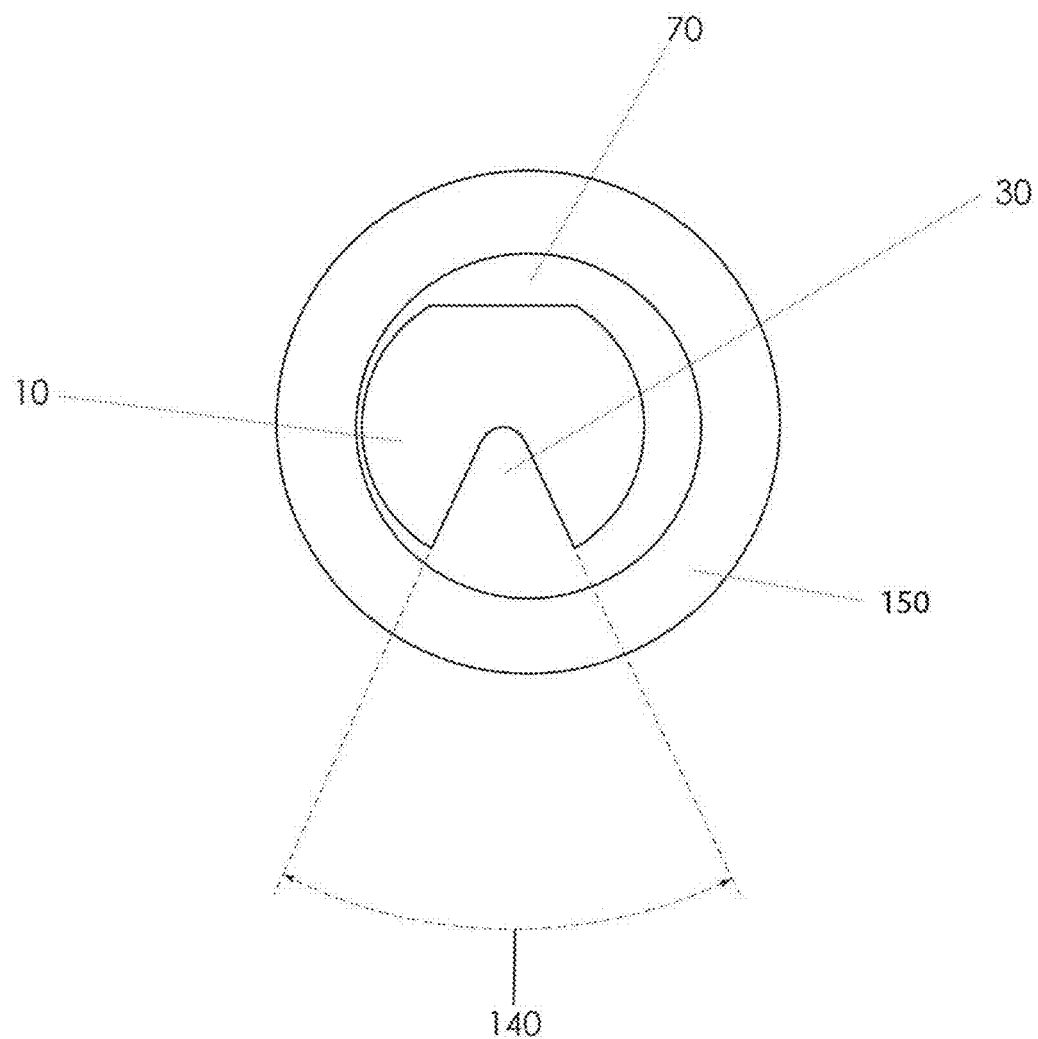
FIG. 6 shows a cross sectional view of an intramedullary canal containing an implantable device.

FIG. 6 shows a sectional representation of an IM canal 70 and cortex 150, containing an implantable device 10 that has been inserted therein. The longitudinal channel 30 has a taper angle 140.

Figure 7:
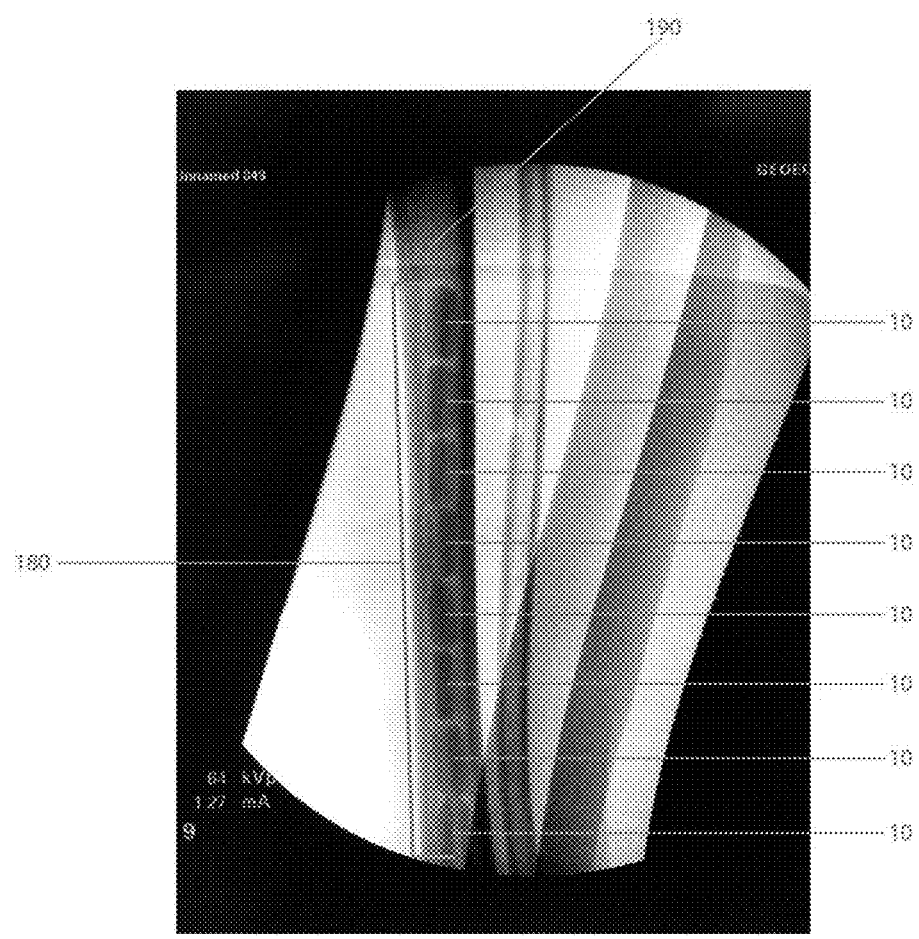
FIG. 7 is an X-ray of a tibia showing the implantable devices contained within the medullary canal.

FIG. 7 shows an X-ray of the tibia 190 of a patient which contains a series of implantable devices 10 lined up end-to-end within the IM canal 180.

It is to be understood that various modifications may be made to the method(s) disclosed herein without departing from the scope of the invention, which may include, but are not limited to, the following:

The method may be directed to treating infected long bone non-unions.

The longitudinal channel cross section may be semi-circular.

The longitudinal channel cross section may be a straight line.

The longitudinal channel may have some other shape.

Bone cement may be used to form the implantable devices.

It is of course to be understood that the present invention is not intended to be restricted to the foregoing examples which are described by way of example only.

EXAMPLES

A long bone medullary canal requiring treatment is prepared as follows:

Ream the canal to the required depth and diameter, the diameter slidingly exceeding the outside diameter of the introducer. An intramedullary canal that has had an intramedullary nail removed may be suitable without the need for reaming. Alternatively, reaming may be required to remove necrotic, infected or cancerous tissues.

Use the flexible mould to produce implantable devices using a bone void filler such as STIMULAN® Rapid Cure (Biocomposites Ltd). Follow the mixing instruction for STIMULAN® Rapid Cure. A typical quantity required to fill an adult subjects' long bone would be about 20 cc when formed into implantable devices according to the instant invention.

Prepare the STIMULAN® Rapid Cure and place the STIMULAN® paste on the area of the mat containing the cavities using the paste applicator.

Once filled, lift the mat and then tap on a solid surface to dislodge and release any trapped air bubbles. Remove excess material from the surface of the mat using the paste applicator or other suitable scraper. Allow the material to set according to the STIMULAN® Rapid Cure instructions and then remove devices from the mat by flexing. Ensure the implantable devices remain in the sterile field. The implantable devices placed end-to-end should be sufficient to fill the IM canal to the required depth. The maximum outside diameter of the implantable devices should be slidingly less than the inside diameter of the guide tube while the outside diameter of the guide tube should be slidingly less than the inside diameter of the reamed IM canal.

Example 1

The implantable device(s) may be digitally inserted, one at a time, in to the IM canal.

Example 2

Load the Guide Tube In Situ

Insert the guide tube in to the IM canal.

Digitally load the guide tube with implantable devices, one at a time, ensuring that the first device added is pushed to the distal end of the guide tube using the pusher and subsequent devices added are pushed forward to abut the previous device. Ensure that the number of devices added is sufficient to fill the IM canal to the required depth.

When the guide tube is populated with sufficient devices, re-insert the pusher to engage the proximal end of the most proximal device.

Apply a positive pressure onto the last implantable device placed into the guide tube using the pusher. Whilst maintaining a positive pressure, pull the guide tube back along the pusher to leave the implantable device(s) in the bone void.

Example 3

Pre-Load the Guide Tube

Digitally load the guide tube with implantable devices, one at a time, ensuring that the first device added is pushed to the distal end of the guide tube and subsequent devices added are pushed forward to abut the previous device. Ensure the number of devices is sufficient to fill the IM canal to the required depth.

Transfer the pre-loaded guide tube to the bone void.

Insert the guide tube slowly into the bone void.

Insert the pusher into the guide tube to engage the most proximal device and apply a light, positive pressure onto the device. Whilst maintaining a positive pressure, pull the guide tube back along the pusher to leave the implantable device(s) in the bone void.

A number of embodiments of the invention have been described. However it is to be understood that various modifications may be made without departing from the scope of the invention.

References:

Akhtar, S., *Fat embolism*. Anesthesiol Clin, 2009. 27(3): p. 533-50.

Issack, P. S., et al., *Fat embolism and respiratory distress associated with cemented femoral arthroplasty*. Am J Orthop (Belle Mead N.J.), 2009. 38(2): p. 72-6.

Shaikh, N., *Emergency management of fat embolism syndrome*. J Emerg Trauma Shock, 2009. 2(1): p. 29-33.

Hampson, F., *Fat embolism*. J Clin Pathol Suppl (R Coll Pathol), 1970. 4: p. 121-2.

Rebellow, M. M., et al., *Venting alone is insufficient in preventing complications in the prophylactic nailing of femoral metastases*, in 49*th Annual Meeting of the Orthopaedic Research Society*. 2003: New Orleans, La., USA.

Knott, L. *Fat Embolism Syndrome*. 2014; Available from: http://patient.info/doctor/fat-embolism-syndrome.

The following is claimed:

1. A method of reconstructing a bone void in a patient, the method comprising introducing into a bone void of one or more implantable devices, each of which one or more implantable devices are substantially cylindrical, having a convex, domed or semi-spherical shaped ends; contain one or more longitudinal channels where the one or more longitudinal channels create a venting path allowing for depressurisation of any contents of the bone void, the one or more longitudinal channels each intersecting a surface of the device and extending towards an axial centerline thereof, and being tapered such that the width of the one or more longitudinal channels opening on an outer, circumferential edge of the implantable device is greater than its width at a base thereof; and have a flat surface on an opposing longitudinal side to the one or more longitudinal channels;

whereby introduction of the one or more implantable devices reconstructs bone in the bone void in the patient.

2. The method of claim 1 where the one or more implantable devices comprise a hardened bone substitute material.

3. The method of claim 1 where the bone void is a contained bone void.

4. A method of claim 2 where the one or more implantable devices are moulded through the use of a multi-cavity flexible mould mat or by 3D printing.

5. A method of claim 1 where the one or more implantable devices are inserted into the bone void by being digitally packed.

6. A method of claim 1 where the one or more implantable devices are inserted into a bone void by the use of an introducer comprising a guide tube and a pusher.

7. A method according to claim 1 where the bone void is a long bone intramedullary canal of a patient.

8. A method according to claim 7 where the bone void is a long bone medullary canal that is reamed out to a diameter to slidingly accept the one or more implantable devices or the guide tube.

9. A method according to claim 7 where the bone void is debrided prior to insertion of the one or more implantable devices.

10. A method according to claim 1 where the one or more implantable devices contains a medicament.

11. A method according to claim 10 where the medicament is an antimicrobial intended to prevent or treat an infection.

12. A method according to claim 11 where the infection is bacterial, fungal or parasitic.

13. A method according to claim 10 where the medicament is an antineoplastic agent for treating a bone tumour, such as a giant cell tumour of bone.

14. A method according to claim 10 where the medicament is a bone morphogenetic protein to aid in bone regeneration.

15. A method of reconstructing a bone void in a patient while reducing pressurisation of the bone void, the method comprising introducing into a bone void of one or more implantable devices through the use of a guide tube and a pusher that facilitates the one or more implantable devices being freely inserted into the intramedullary canal; where the one or more implantable devices comprise: 1) a capsule shape, having convex, domed or semispherical shaped ends; and 2) one or more longitudinal channels extending the entire length of the implantable device;

wherein the one or more longitudinal channels create a venting path allowing for the depressurization of any contents of the bone void, the one or more longitudinal channels each intersecting a surface of the device and extending towards an axial centerline thereof, and being tapered such that the width of the one or more longitudinal channels opening on an outer, circumferential edge of the implantable device is greater than its width at a base thereof, and have a flat surface on an opposing longitudinal side to the one or more longitudinal channels;

whereby introduction of the one or more implantable devices reconstructs bone in the bone void while reducing pressurisation of the bone void in the patient.

* * * * *